US00PP21579P3

(12) United States Plant Patent
Arias

(10) Patent No.: US PP21,579 P3
(45) Date of Patent: Dec. 21, 2010

(54) TANGERINE TREE NAMED 'PARGA NO. 2'
(50) Latin Name: ***Citrus reticulata* blanco**
Varietal Denomination: Parga No. 2

(75) Inventor: Silvestre Arias, Fresno, CA (US)
(73) Assignee: Parga Partners

( * ) Notice: Subject to any disclaimer, the term of this patent is extended or adjusted under 35 U.S.C. 154(b) by 58 days.
(21) Appl. No.: 12/321,207
(22) Filed: Jan. 15, 2009
(65) Prior Publication Data
US 2010/0170018 P1 Jul. 1, 2010
Related U.S. Application Data
(63) Continuation of application No. 12/347,901, filed on Dec. 31, 2008.
(51) Int. Cl.
*A01H 5/00* (2006.01)
(52) U.S. Cl. ..... Plt./201
(58) Field of Classification Search ..... Plt./201
See application file for complete search history.
*Primary Examiner*—Kent L Bell
(74) *Attorney, Agent, or Firm*—Mark D. Miller

(57) ABSTRACT

A new distinct variety of tangerine tree characterized by producing a small to medium size fruit that is mature for harvesting and shipping in mid October about nine to ten days earlier than 'Clementine' mandarin and with good flavor.

1 Drawing Sheet

(*Citrus reticulata* blanco)

BACKGROUND OF THE NEW VARIETY

In the fall of 2007, the inventor observed a single tree of 'Clementine' mandarin (*Citrus reticulata* blanco) that was fully colored and mature nine to ten days earlier than the other 'Clementine' mandarin trees in a 40-acre orchard in an area just south of the City of Fresno, Calif., in the San Joaquin Valley of Central California. This single tree on C-35/Citrange rootstock, *Ponicrus trifoliate*×*Citrus sinensis*, produced a heavy crop in the fourth year (2008) with the fruit varying in size from small to medium, yellow-orange color when fully ripe with sugar content of 11% at maturity, October 14-18, with a pleasant flavor.

ORIGIN AND ASEXUAL REPRODUCTION OF THE NEW VARIETY

The new variety of *Citrus reticulata* blanco is a naturally occurring bud sport of 'Clementine' mandarin. The sport of 'Clementine' mandarin was observed in 2007 because of its continuing earlier maturity and harvest than the original 'Clementine' mandarin while maintaining its distinguishing characteristics. The new variety was bud grafted onto 'Citrange' rootstock and produced at a site near the corner of Clovis and North Avenues, in Fresno County, Calif.

SUMMARY OF THE NEW VARIETY

'Parga No. 2 ' is characterized by producing a small to medium yellow-orange fruit with a pleasant flavor and good productive capacity that matures for harvesting and shipment October 14-18 in the Fresno area of the San Joaquin Valley in a normal year. This variety can be compared to 'Clementine' mandarin but matures nine to ten days earlier.

Figure 1:
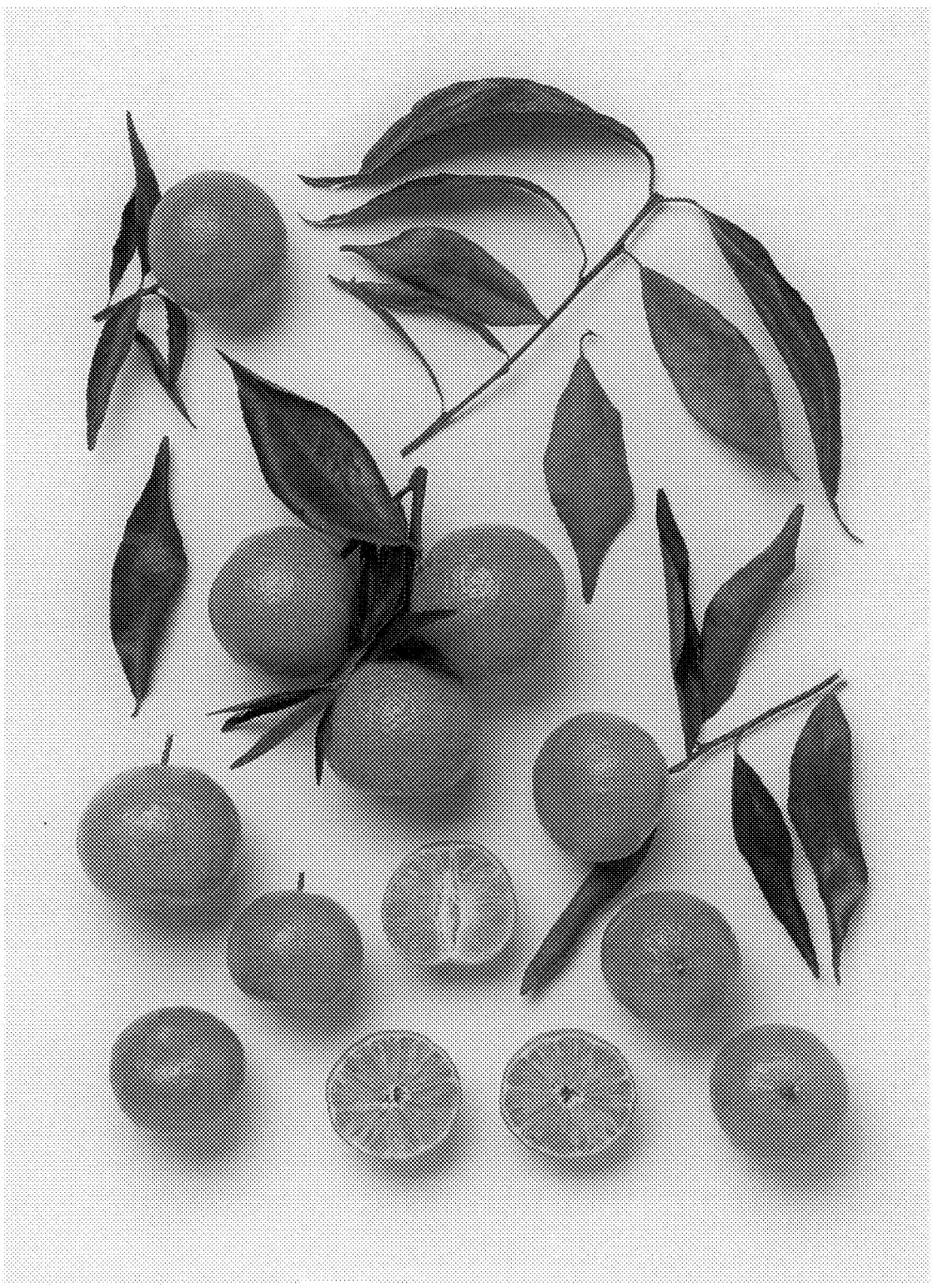
FIG. 1 is a color photograph of the new variety displaying a fruit attached to a twig and several leaves across the top and to the left followed on the right by a young branch with leaves attached displaying upper and lower surfaces.

Directly below is a cluster of three fruits attached to a young branch with several leaves.

To the right is a side view of a fruit attached to a young branch and leaves.

Across the lower part of the photograph are two rows of fruit. On the upper row and to the left is a side view of fruit and stem attached, and to the right a smaller fruit. Then to the right is a fruit cut in half along center displaying the flesh followed by a bottom view of the fruit on the right.

On the bottom row is a side or lateral view of fruit followed by two halves displaying the segments of the flesh of the fruit. Finally, on the right is a fruit displaying the top view.

DETAILED DESCRIPTION

Referring more to the horticultural description of the new and distinct variety of Mandarin tangerine, the following description has been observed under the ecological conditions prevailing at the origin orchard which is located near the City of Fresno in the San Joaquin Valley of Central Calif. A four year old tree was observed. All major color descriptions are by reference to the Dictionary of Color by Maerz & Paul, First Edition, published in 1930. Common colors are also employed.

TREE

The new variety of the present application is generally medium in size.

*Height.*—8-10 feet (244-304 cm).
*Width.*—8 feet (244 cm).
*Vigor.*—Very good.
*Figure.*—Upright with a spreading shape.
*Productivity.*—Very good.
*Regularity of Bearing.*—Regular.

Lenticels:

*Number.*—3-4 per square cm.
*Length.*—⅓ inch.

*Diameter.*—⅛ inch.
*Color.*—Pompenian R (4-J-10).

TRUNK

Size: 13 inch (33.02 cm) circumference, 8 inches (20.32 cm) above ground level, 4 inches (10.16 cm) above graft
Color: Mauve Taupe Copra (7-C-8)
Surface texture: Slightly rough

BRANCHES

Size: Medium, 3-4 inches (7.62-10.16 cm) in circumference at approximately 4 years
Bark surface texture: Smooth
Bark color:
*Mature.*—Mt. Vernon Green (23-J-8).
*Immature* (*less than one year*).—Cossack green (23-J-11).
Crotch Angle: Approximately 57°

LEAVES

Size: Large for Mandarin group
Length: 4.33-4.72 inches (11.00-12.00 cm)
Width: 1.46-1.89 inches (3.71-4.80 cm)
Shape: Elliptic to oblong
Arrangement: In clusters of 8-10
Color:
*Upper surface.*—Evergreen (24-E-12).
*Lower surface.*—Art gr. (22-L-7).
Petiole:
*Length.*—0.39 inch (0.99 cm).
*Diameter.*—10 mm.
*Petiole color.*—Cypress Green (28-L-6) +Forest Green (23-L-6)
Leaf marginal form: Slightly serrated.
Leaf vein color: Cosse Gr. (19-L-5)
Numbers: Many
Surface texture: Smooth
Thickness: 0.08 inch (2 mm).
Stem glands: None

FLOWERS

Flower Buds:
*Size.*—Small, diameter range of 0-2.00 inches, (0-5.08 cm).
*Shape.*—Conic.
*Surface texture.*—Nearly smooth.
Flowers generally showy, 4-6 flowers per cluster.
Date of first bloom: April 25
Date of full bloom: May 7
Flowers:
*Diameter.*—0.79-0.91 inches (2.0-2.3 cm).
*Petals.*—4-5 Petal Color (upper and lower surfaces): White (1-A-1) Petal Length: 0.16-0.20 inch (0.41-0.51 cm) Petal Width: 0.08-0.11 inches (0.20-0.28 cm) Apex: _rounded Margin: entire Base: rounded.
Pedicel:
*Lengths.*—0.14-0.20 inch (0.36-0.51 cm).
*Color.—Popcorn (*9-J-3).
Number of sepals: 4-5
*Color(upper and lower surfaces).*—Endive (17-L-3).
*Margin.*—_rounded.
Stamens: 13-14
Filament color: White (1-A-1).
Anthers: Small
*Color.*—Cavalry, Deep Chrome Y (9-L-7).
Pistil length: 0.28 - 0.31 inch (0.71-0.79 cm)
*Color.*—Apricot Y. (9-K-5).
Fragrance: Mild.
Pollen color: Yellow (1-A-10)

FRUIT

Date of maturity: Mid October
Typical fruit weight: 4.92 grams (3.91 oz.)
Typical tree production: Approx. 300 lbs
Size: small
*Average height.*—1.75 inch (4.45 cm).
*Average width.*—1.74 inch (4.42 cm).
*Average weight.*—3.91 ounces (110.85 grams).
Size: Medium
*Average height.*—2.43 inches (6.17 cm).
*Average width.*—2.52 inches (6.40 cm).
*Average weight.*—4 ounces (113.40 grams).
Form: Globose to oblong
Stem:
*Diameter.*—0.20 inch (0.51 cm).
*Length.*—0.19-0.20 inch (0.48-0.51 cm).
*Color.—Eden Gr (*20-L-9).
Rind:
*Color.*—Cadmium Y (9-L-8).
*Thickness.*—Average 0.0 -0.16 inch (0.20-0.41 cm).
*Surface.*—Slightly pebbled to rugose.
Oil cells:
*Number.*—40-50 per sq cm.
Albedo:
*Thickness.*—2-4 mm (0.08-0.16 in).
*Color.*—Hydrangea Pk Aurore (2-E-7).
Segments: Flesh is 12-14 regularly separated segments
*Vesicles.*—Globose to obovoid.
*Flesh Color.*—Golden glow (9-L-6).
*Skin.*—Tender.
*Pulp Color.*—Uniform Calvary Deep Chrome $Y^P$ (9-L-7).
Juice:
*Flavor.*—Very good.
*Quantity.*—Moderate.
*Color.*—Empire Y. (9-K-3).
*Sugar.*—11%
*Sugar Acid Ratio.*—12.0
Seeds: Seedless
Tree storage: Fruit hangs well on the tree
Use: Fresh market
Keeping quality: Excellent
Shipping quality: Excellent
Resistance to disease: No disease observed The above description of a new variety of 'Clementine' mandarin is based on growing conditions in the Central San Joaquin Valley of California. Variations of the usual magnitude such as differences in maturity dates and production may be due to cultural activities such as irrigation, fertilization, pruning and climatic change.

What is claimed is:

1. A new distinct variety of tangerine tree characterized by producing a small to medium size fruit that is mature for harvesting and shipping in mid October about nine to ten days earlier than 'Clementine' mandarin and with good flavor.

* * * * *